United States Patent
Lassus et al.

(10) Patent No.: US 12,233,131 B2
(45) Date of Patent: Feb. 25, 2025

(54) CATIONIC CALIBRATED-SIZE GAS-FILLED MICROVESICLES

(71) Applicant: Bracco Suisse SA, Cadempino (CH)

(72) Inventors: Anne Lassus, Carouge (CH); Samir Cherkaoui, Feigeres (FR)

(73) Assignee: Bracco Suisse SA, Cadempino (CH)

( * ) Notice: Subject to any disclaimer, the term of this patent is extended or adjusted under 35 U.S.C. 154(b) by 0 days.

(21) Appl. No.: 18/565,586

(22) PCT Filed: Jul. 14, 2022

(86) PCT No.: PCT/EP2022/069809
§ 371 (c)(1),
(2) Date: Nov. 30, 2023

(87) PCT Pub. No.: WO2023/285628
PCT Pub. Date: Jan. 19, 2023

(65) Prior Publication Data
US 2024/0277866 A1    Aug. 22, 2024

(30) Foreign Application Priority Data

Jul. 14, 2021 (EP) .................... 21185579

(51) Int. Cl.
| | |
|---|---|
| A61K 47/69 | (2017.01) |
| A61K 47/10 | (2017.01) |
| A61K 47/24 | (2006.01) |
| A61K 48/00 | (2006.01) |

(52) U.S. Cl.
CPC .......... *A61K 47/6925* (2017.08); *A61K 47/10* (2013.01); *A61K 47/24* (2013.01); *A61K 48/0041* (2013.01)

(58) Field of Classification Search
None
See application file for complete search history.

(56) References Cited

U.S. PATENT DOCUMENTS

2007/0081946 A1* 4/2007 Schneider .......... A61K 47/6925
977/929

FOREIGN PATENT DOCUMENTS

| WO | 2018041906 A1 | 3/2018 |
| WO | 2019170606 A1 | 9/2019 |
| WO | 2020260420 A1 | 12/2020 |
| WO | 2020260423 A1 | 12/2020 |

OTHER PUBLICATIONS

Es, Ismail, "Microfludic platforms based on chaotic mixing and diffusion for complexation of cationic liposome and pDNA," VII Workshop em Microfluidica, pp. 1-2 (2017).
Fenske, D.B, et al., "Cationic poly(ethyleneglycol) lipids incorporated into pre-formed vesicles enhance binding and uptake to BHK cells," Biochimica et Biophysica Acta, 1512:259-272 (2001).
Hattori, Y., et al., "Effects of PEG anchors in PEGylated siRNA lipoplexes on in vitro gene-silencing effects and siRNA biodistribution in mice," Molecular Medicine Reports, 22:4183-4196 (2020).
International Search Report and Written Opinion for PCT/EP2022/069809, mailed Nov. 9, 2022.
Ja'Affar, F., et al., "Surface Charge Measurement of SonoVue™, Definity™ and Optison™: a comparison of Laser Doppler Electrophoresis and Micro-Electrophoresis," 41(11):2990-3000 (2015).
Wang, D.S., et al., "Cationic versus Neutral Microbubbles for Ultrasound-mediated Gene Delivery in Cancer," Radiology, 264(3):721-732 (2012).

* cited by examiner

*Primary Examiner* — Robert A Wax
*Assistant Examiner* — Andre Mach
(74) *Attorney, Agent, or Firm* — VIVICAR Law, PLLC

(57) ABSTRACT

Technical field The invention relates to new calibrated-size gas-filled microvesicles bearing an overall positive charge, to their use and to their method of manufacturing. The gas-filled microvesicles have a geometric standard deviation (GSD) value of at least 1.25 or lower and a stabilizing envelope comprising an amphiphilic material, said amphiphilic material comprising a cationic lipid and a neutral or cationic amphiphilic polymeric compound.

18 Claims, 2 Drawing Sheets

CATIONIC CALIBRATED-SIZE GAS-FILLED MICROVESICLES

CROSS-REFERENCE TO RELATED APPLICATIONS

This application is the national stage application of corresponding international application number PCT/EP2022/069809, filed Jul. 14, 2022, which claims priority to and the benefit of European application no 21185579.6, filed Jul. 14, 2021, which is hereby incorporated by reference in its entirety.

TECHNICAL FIELD

The invention relates to new calibrated-size gas-filled microvesicles bearing an overall positive charge, to their use and to their method of manufacturing.

BACKGROUND OF THE INVENTION

Calibrated-size gas-filled microvesicles (in short "calibrated microvesicles" or "CMV") are a new generation of gas-filled microvesicles having a relatively narrow and controlled size distribution (with mean diameter sizes which can be selected to range between 2 and 8 μm), as compared to commercially available polydisperse microbubble ultrasound contrast-agents (USCA). Calibrated microvesicles are in particular designed to enhance imaging sensitivity and improve efficiency in therapeutic treatments, e.g. in delivering drugs or genes to specific organs through different techniques, including, for instance, BBB (Blood Brain Barrier) disruption, thermal ablation, sonopermeabilisation or sonothrombolysis. Calibrated microvesicles can be produced using various techniques: decantation, mechanical filtration, centrifugation, bubble sorting and flow-focusing. Particularly, the flow-focusing technology allows the manufacturing of calibrated microvesicles (characterized by a relatively low value of geometric standard deviation (GSD), e.g. down to about 1.05-1.08) in a highly reproducible way at a reasonable production rate ($\sim 10^6$ bubbles per second), with acceptable concentrations of suspended microvesicles (e.g. up to $4 \times 10^8$ CMV/mL) for subsequent uses. WO2018/041906 (Ref. 1) and WO2019/170606 (Ref. 2), describe suitable methods for preparing CMV, in particular by using flow-focusing microfluidic techniques.

While gas-filled microvesicles comprising cationic amphiphilic compounds are generally known in the art (see e.g. Ref. 5: Wang et al., "Cationic versus Neutral Microbubbles for Ultrasound-mediated Gene Delivery in Cancer", Radiology: Volume 264: Number 3 Sep. 2012, pp 721-732), Applicant is not aware of any attempt to prepare calibrated gas-filled microvesicles, in particular by flow-focusing microfluidic techniques, comprising such cationic amphiphilic material, and particularly cationic lipids.

The Applicant has however observed that the presence of certain lipid derivatives of a polyethylene glycol ("PEG") in the formulation of the microvesicles, which may otherwise be useful for providing desirable physicochemical properties to the stabilizing layer of the microvesicles, as well as for limiting coalescence phenomena in the freshly produced CMV, may nevertheless undesirably affect other physicochemical properties of the microvesicles. In particular, the Applicant has observed that the use of negatively charged pegylated phospholipids for preparing the CMV with the flow-focusing method may substantially reduce or prevent the incorporation of the cationic lipids in the stabilizing layer of the CMV, with the result that the overall net charge of the microvesicles is not sufficiently positive (e.g. to effectively bind negatively charged genetic material).

SUMMARY OF THE INVENTION

An aspect of the invention relates to a suspension of gas-filled microvesicles with a stabilizing envelope comprising an amphiphilic material, wherein said amphiphilic material comprises a cationic lipid and a neutral or cationic amphiphilic polymeric compound, said amphiphilic polymeric compound comprising a respective hydrophilic and a hydrophobic portion and being present in a molar amount higher than 3%, and wherein said gas-filled microvesicles have a geometric standard deviation (GSD) value of at least 1.25 or lower.

The suspension of calibrated microvesicles preferably has a GSD of at least 1.22 or lower, more preferably of at least 1.20.

The cationic lipid is preferably a compound comprising a saturated or unsaturated $C_8$-$C_{24}$ hydrocarbon chain linked to an ammonium group, in particular a quaternary amine or a protonated tertiary amine group. The cationic lipid is preferably a cationic phospholipid, a $C_8$-$C_{24}$ fatty acid derivative of ammonium or a $C_8$-$C_{24}$ alkyl or alkyloxy derivative of ammonium. For instance, the cationic lipid is a $C_8$-$C_{24}$ fatty acid derivative of ethyl phosphatidylcholine, a $C_8$-$C_{24}$ fatty acid derivative of trimethylammonium or a $C_8$-$C_{24}$ alkyl or alkyloxy chain bound to a quaternary or to a protonated tertiary ammonium group.

The amphiphilic polymeric compound is preferably present in a molar amount of at least 5%, more preferably of at least 7.5%.

Said amphiphilic polymeric compound is preferably neutral. The hydrophilic portion preferably comprises a hydrophilic polymer, such as polyethylene glycol ("PEG"). The hydrophobic portion preferably comprises an alkyl. Alternatively, the hydrophobic portion comprises a hydrophobic polymer, such as oxypropylene repeating units.

In certain embodiments, the amphiphilic polymeric compound is an ester of polyethylene glycol with a $C_{12}$-$C_{24}$ fatty acid. The fatty acid forming the ester with the polyethylene glycol is preferably a $C_{14}$-$C_{20}$ fatty acid, such as myristic acid, palmitic acid, stearic acid, arachidic acid, linoleic acid, linolenic acid or oleic acid. In certain other embodiments, the alkyl-modified polyalkylene comprises a $C_{12}$-$C_{24}$ alkyl linked to the polyalkylene glycol.

In another embodiment, the neutral or cationic amphiphilic polymeric compound is a block copolymer, preferably comprising a hydrophobic portion and a hydrophilic portion. In a preferred embodiment, said block copolymer comprises repeating oxypropylene units and repeating oxyethylene units.

The molecular weight of the amphiphilic polymeric compound is preferably from 1000 to 9000 g/mol, more preferably of from 1500 to 6000 g/mol and even more preferably of from 1800 to 5000 g/mol.

The CMV may further comprise a neutral lipid, e.g. a phospholipid or a fatty acid, in addition to the cationic lipid and to the neutral or cationic amphiphilic polymeric compound. The neutral lipid is preferably a phospholipid, more preferably a $C_{12}$-$C_{24}$ fatty acid derivative of phosphatidylcholine or of phosphatidylethanolamine.

CMV as above defined typically have an overall positive charge on their surface, which can be expressed as "zeta-potential". CMV according to the invention have a zeta-potential of at least 10 mV or higher, preferably of at least 12 mV or higher and even more preferably of at least 15 mV or higher.

CMV according to the invention can be prepared by:
providing (i) a gaseous flow and (ii) an aqueous liquid flow comprising a cationic lipid, a neutral or cationic amphiphilic polymeric compound and optionally a neutral lipid;
directing said gaseous flow and said liquid flow through respective inlet channels towards a contact zone;
directing said gaseous flow and said liquid flow from the contact zone through a calibrated orifice to obtain an aqueous suspension comprising said gas-filled microvesicles;
directing said suspension of gas-filled microvesicles towards an outlet channel; and
collecting said suspension of gas-filled microvesicles.

Another aspect of the invention relates to CMV prepared according to the above method.

A further aspect of the invention relates to the use of calibrated gas-filled microvesicles as defined above in a method of diagnosing Another aspect of the invention relates to the use of calibrated gas-filled microvesicles as defined above in a method of ultrasound therapeutic treatment In an embodiment, said method of ultrasound therapeutic treatment comprises:
(i) administering to a patient a suspension of CMV according to the invention;
(ii) identifying a region of interest in said patient to be submitted to a therapeutic treatment, said region of interest comprising said suspension of CMV; and
(iii) applying an ultrasound beam for therapeutically treating said region of interest;
whereby said ultrasound therapeutic treatment is enhanced by the presence of said suspension of CMV in said region of interest.

In another embodiment said method of ultrasound therapeutic treatment comprises:
(i) administering to a patient a suspension of CMV according to the invention which are bound to a therapeutically effective material bearing an overall negative charge;
(ii) identifying a region of interest in said patient in need of said therapeutic treatment, said region of interest comprising said suspension of said bound CMV; and
(iii) applying an ultrasound beam for therapeutically treating said region of interest, said treating comprising the release of the therapeutically active material in the region of interest.

FIGURES

DETAILED DESCRIPTION OF THE INVENTION

Definitions

Figure 1:
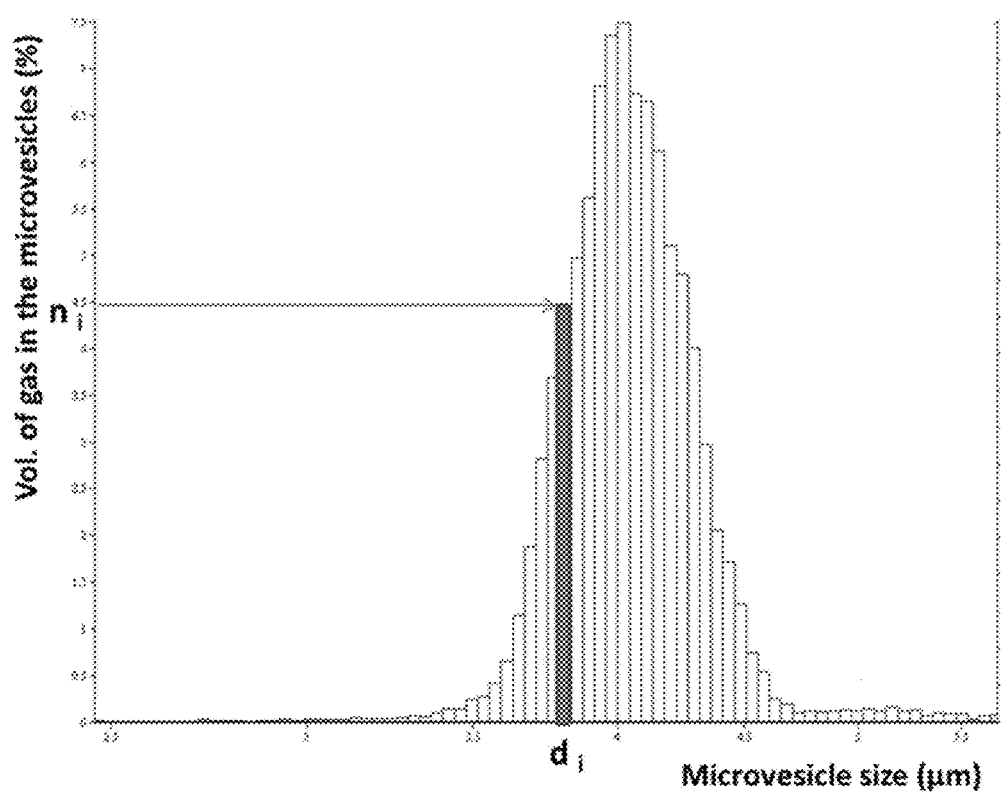
FIG. 1 shows a typical particle size distribution representation.

As used herein the term "cationic lipid" refers to an amphiphilic material bearing an overall positive charge on its molecule. Amphiphilic materials include in their molecule a hydrophilic portion (e.g. bearing a polar or ionic group) and a hydrophobic portion (e.g. a hydrocarbon chain, e.g. $C_8$-$C_{24}$). The positive charge may derive from a suitable cationic group, e.g. ammonium, in the amphiphilic molecule. Cationic lipids can generally be employed as salts with suitable negative counterions (e.g. halides, such as chloride or bromide, or sulfates, such as methyl sulfate); for instance, when the amphiphilic molecule contains ammonium, the molecule may thus be in the form of a corresponding ammonium salt with an halide. Cationic lipids include, for instance, quaternary amines or ionizable (protonated) tertiary amines linked to saturated or unsaturated hydrocarbon chains.

As used herein, the expression "neutral or cationic amphiphilic polymeric compound" refers to a polymeric compound comprising a hydrophobic and a hydrophilic portion and bearing an overall neutral or positive net charge. Typically, the hydrophobic portion is capable of interacting (e.g. via non-covalent interactions, typically hydrophobic interactions) with the other components forming the stabilizing envelope of the gas-filled microvesicles and is positioned towards the inner core of the microvesicles (in contact with the gas) while the hydrophilic portion is positioned on the outer portion of the shell, to interact with the liquid of the suspension. The hydrophilic portion can be, for instance, a polymer comprising repeating units forming a hydrophilic polymer, such as oxyethylene units. In preferred embodiments, said hydrophilic portion is polyoxyethylene.

In certain embodiments, the hydrophobic portion of the neutral or cationic amphiphilic polymeric compound is an alkyl chain, for instance ($C_{10}$-$C_{30}$) alkyl, preferably $C_{12}$-$C_{26}$, more preferably $C_{14}$-$C_{20}$. The term alkyl comprises linear, branched or cyclic alkyl chains, as well as saturated or unsaturated alkyl chains. The alkyl chain can be linked directly to the polymeric portion or through suitable functional groups, such as an ether, ester and/or amide group. The neutral or cationic amphiphilic polymeric compound is thus referred to as a "neutral or cationic alkyl-modified (or "alkyl-containing") polymer". For instance, when the alkyl chain is a fatty residue, it can be linked to the polymeric portion through an ester group.

In certain other embodiments the hydrophobic portion of the neutral or cationic amphiphilic polymeric compound is a polymer comprising repeating units forming a hydrophobic polymer. For instance, said repeating units can be oxypropylene, e.g. from 20 to 60 units, preferably from 30 to 50 units.

The expression "gas-filled microvesicles" generally refers to bubbles of gas bounded, at the gas/liquid interface, by a very thin envelope (film) involving a stabilizing amphiphilic material (e.g. a lipid, typically a phospholipid) disposed at the gas to liquid interface. Said calibrated gas-filled microvesicles are suitable as contrast agents in ultrasound imaging techniques, known as Contrast-Enhanced Ultrasound (CEUS) Imaging, or in therapeutic applications, e.g. in combination with ultrasound mediated drug delivery.

These stabilized gas bubbles (dispersed in a suitable physiological solution) are generally referred to in the art with various terminologies, depending typically on the stabilizing material employed for their preparation; these terms include, for instance, "microspheres", "microbubbles", "microcapsules" or "microballoons", globally referred to here as "gas-filled microvesicles" (or "microvesicles" in short).

The term "calibrated" (when referred to gas-filled microvesicles) specifically refers to microvesicles suspensions with highly calibrated microvesicles (CMV), having different sizes between 2 and 8 μm, characterized by a size distribution having a geometric standard deviation (GSD) of at least 1.25 or lower, preferably of at least 1.2, more preferably of at least 1.1, down to e.g. 1.05.

Calibrated gas-filled microvesicles are preferably produced by using a microfluidic flow-focusing technology, where a gas thread is focused between two liquid flows comprising an amphiphilic material (e.g. a lipid) in a flow-focusing device, to form lipid-stabilized calibrated microvesicles which are then collected as an aqueous suspension of CMV (in a vial pre/filled with respective gas) at the exit of an outlet channel, as described for instance in the above cited Refs. 1 and 2.

Components of Microvesicles

Positively charged gas-filled microvesicles according to the invention can be manufactured by using a formulation comprising a cationic lipid and a neutral or cationic amphiphilic polymeric compound. The microvesicles may further comprise neutral lipids, such as neutral phospholipids and/or fatty acids, in admixture with the above cationic lipid and neutral or cationic amphiphilic polymeric compound.

Cationic Lipids

Cationic lipids may include, for instance, cationic lipids with saturated or unsaturated hydrocarbon (alkyl) chains (which may contain carboxylic and/or ether groups) linked to an ammonium group, i.e. a quaternary amine or an ionizable (protonated) tertiary amine group. Preferably the cationic lipid is a monovalent cation. Examples of lipids linked to an amine group include, for instance, $C_8$-$C_{24}$ phospholipid derivatives of ammonium; $C_8$-$C_{24}$ fatty acid derivatives of ammonium; $C_8$-$C_{24}$ alkyl derivatives of ammonium; or $C_8$-$C_{24}$ alkyloxy (typically an oxygen-terminated alkyl chain) derivatives of ammonium. The further residues bound to the quaternary or ternary amine groups are preferably ($C_1$-$C_6$) alkyl, more preferably ($C_1$-$C_4$) alkyl and even more preferably methyl. As mentioned, such cationic lipid may be employed as salts, preferably halide, e.g. chloride or bromide.

Fatty acids (either as a compound as such or as a derivatized residue thereof, e.g. an ester) may include $C_{10}$-$C_{24}$, preferably $C_{12}$-$C_{22}$, more preferably $C_{14}$-$C_{20}$ carboxyl terminated hydrocarbon chains. These may include saturated fatty acids, such as lauric (n-dodecanoic), myristic (n-tetradecanoic), palmitic (n-hexadecanoic), stearic (n-octadecanoic), arachidic (n-eicosanoic), behenic (n-docosanoic), or unsaturated fatty acids of similar chain lengths such as decenoic, dodecenoic, tetradecenoic, hexadecenoic, hexadecadienoic, octadecenoic, octadecadienoic, octadecatrienoic, octadecatetraenoic, eicosenoic, eicosadienoic, eicosatrienoic, eicosatetraenoic, eicosapentaenoic, docosaenoic, docosadienoic, docosatrienoic, docosatetraenoic and docosapentaenoic, preferably myristoleic (cis-9-tetradecenoic), palmitoleic (cis-9-hexadecenoic), sapienic (cis-6-hexadecenoic), oleic (cis-9-octadecenoic), linoleic (cis-9,12-octadecadienoic), linolenic (cis-9,12,15-octadecatrienoic), gondoic (cis-11-eicosenoic), cis-11,14-eicosadienoic, cis-5,8,11-eicosatrienoic, cis-8,11,14-eicosatrienoic, cis-11,14,17-eicosatrienoic, arachidonic (cis-8,11,14,17-eicosatetraenoic) and erucic (cis-13-docosenoic) acid.

Cationic phospholipids may include, for instance, $C_{10}$-$C_{24}$ fatty acid derivatives (e.g. esters), preferably $C_{12}$-$C_{22}$, more preferably $C_{14}$-$C_{20}$, of phosphatidylcholine, preferably of ethyl phosphatidylcholine. Preferably said cationic phospholipid is a compound of general formula (I):

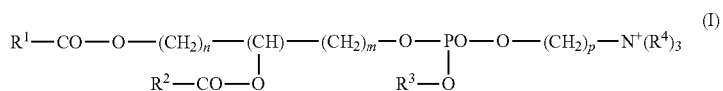

where:
- $R^1$ and $R^2$ each independently represent a $C_9$-$C_{23}$, preferably $C_{11}$-$C_{21}$, more preferably $C_{13}$-$C_{19}$ saturated or unsaturated alkyl chain;
- $R^3$ represents a $C_1$-$C_4$, preferably $C_2$-$C_3$ alkyl chain, more preferably ethyl; and
- each of the three $R^4$ independently represents a $C_1$-$C_4$, preferably $C_1$-$C_2$ alkyl chain, more preferably methyl;
- n is an integer of from 1 to 4, preferably 1 or 2, more preferably 1;
- m is an integer of from 0 to 4, preferably 1 or 2, more preferably 1; and
- p is an integer of from 1 to 4, preferably 2 or 3, more preferably 2.

Cationic phospholipids can be used, for instance, as chloride or bromide salt.

Examples of such cationic phospholipids include, for instance, dilauroyl-sn-glycero-3-ethylphosphocholine (DLePC), dimyristoyl-sn-glycero-3-ethylphosphocholine (DMePC), dipalmitoyl-sn-glycero-3-ethylphosphocholine (DPePC), diarachidoyl-sn-glycero-3-ethylphosphocholine (DAePC), distearoyl-sn-glycero-3-ethylphosphocholine (DSePC), dioleoyl-sn-glycero-3-ethylphosphocholine (DOePC), dipentadecanoyl-sn-glycero-3-ethylphosphocholine (DPDePC), 1-myristoyl-2-palmitoyl-sn-glycero-3-ethylphosphocholine (MPePC), 1-palmitoyl-2-myristoyl-sn-glycero-3-ethylphosphocholine (PMePC), 1-palmitoyl-2-stearoyl-sn-glycero-3-ethylphosphocholine (PSePC), 1-stearoyl-2-palmitoyl-sn-glycero-3-ethylphosphocholine (SPePC), 1-palmitoyl-2-oleyl-sn-glycero-3-ethylphosphocholine (POePC) and 1-oleyl-2-palmitoyl-sn-glycero-3-ethylphosphocholine (OPePC).

Fatty acid derivatives of (alkyl)ammonium (particularly alkyl-ammonium) may include, for instance, ($C_8$-$C_{24}$) fatty acid derivatives (preferably $C_{12}$-$C_{22}$, more preferably $C_{14}$-$C_{20}$, particularly preferred being $C_{16}$-$C_{18}$ derivatives) of ammonium (e.g. as chloride or bromide salt, or as methyl sulfate salt). Preferably, said fatty acids derivative of ammonium is a compound of general formula (II), (IIa) or (IIb):

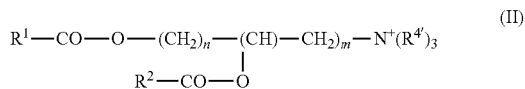

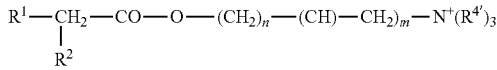

(IIa)

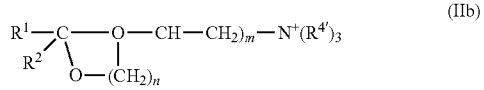

(IIb)

where:

R$^1$, R$^2$, m and n have the same meanings as above and R$^{4'}$ independently represents hydrogen or a C$_1$-C$_4$, preferably C$_1$-C$_2$ alkyl chain, more preferably methyl, with the proviso that at most one R$^{4'}$ residue is hydrogen.

Examples of such (C$_8$-C$_{24}$) fatty acid derivatives of ammonium include, for instance, 1,2-distearoyl-3-trimethylammonium-propane (DSTAP), 1,2-dioleoyl-3-trimethylammonium-propane (DOTAP), 1,2-dimyristoyl-3-trimethylammonium-propane (DMTAP), 1,2-dipalmitoyl-3-trimethylammonium-propane (DPTAP), 1,2-distearoyl-3-dimethylammoniumpropane (DSDAP), and (N-(4-carboxybenzyl)-N,N-dimethyl-2,3-bis(oleoyloxy)propan-1-aminium (DOPAQ), (6Z,9Z,28Z,31Z)-Heptatriaconta-6,9,28,31-tetraen-19-yl 4-(dimethylamino) butanoate (DLin-MC3-DMA) or 2-[2,2-bis[(9Z,12Z)-octadeca-9,12-dienyl]-1,3-dioxolan-4-yl]-N, N-dimethylethanamine (DLin-KC2-DMA).

Alkyl or alkyloxy derivatives of ammonium may include, for instance, compounds comprising one or preferably two C$_{10}$-C$_{24}$ alkyl or alkyloxy chains (preferably C$_{12}$-C$_{22}$, more preferably C$_{14}$-C$_{20}$, particularly preferred being C$_{16}$-C$_{18}$ derivatives, bound to a quaternary or to a protonated tertiary ammonium group. Preferably said alkyl or alkyloxy derivative of ammonium is a compound of formula (III) or (IV), respectively:

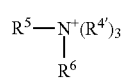

(III)

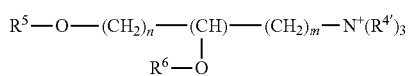

(IV)

Where:

n and m have the same meaning as above;

R$^5$ and R$^6$ each independently represent a C$_{10}$-C$_{24}$, preferably C$_{12}$-C$_{22}$, more preferably C$_{14}$-C$_{20}$ alkyl chain;

R$^{4'}$ is as defined above.

Examples of such alkyl or alkyloxy derivatives of ammonium include, for instance, dimethyldioctadecylammonium (DDAB), 1,2-di-O-octadecenyl-3-trimethylammonium propane (DOTMA), 1,2-dioleyloxy-3-dimethylaminopropane) DODMA.

Multivalent cationic lipids include, for example, dioctadecylamidoglycylspermine (DOGS).

As used herein, the term "alkyl (or hydrocarbon) chain" includes linear or branched, saturated or unsaturated alkyl (hydrocarbon) chains.

Concerning cationic lipids with (saturated or unsaturated) hydrocarbon chains linked to a ionizable tertiary amine group, the respective pKa value of such cationic lipids should be sufficiently high as to allow protonation in relatively acidic in vivo environments (e.g. an endosome, pH 5.5-6.5); on the other hand, it shall by low enough to make lipid substantially compatible with physiological pH (i.e. about 7.4). Preferably, the pka value of cationic lipids is of at least 5 or higher, more preferably of at least 6 or higher. Said pKa value shall preferably be lower than 8, more preferably lower than 7.5.

Amphiphilic Polymeric Components

Amphiphilic polymeric components suitable for preparing gas-filled microvesicles according to the invention may include, for instance, repeating oxyalkylene units, such as oxypropylene or oxyethylene. The amphiphilic polymeric compound may thus include polyalkylene glycols, such as polyethylene glycols or polypropylene glycols, preferred being polyethylene glycol. Examples of suitable amphiphilic polymeric components include neutral or cationic alkyl-modified polyethylene glycols or block copolymers comprising a polyethylene glycol (i.e. repeating units of oxyethylene).

The number of oxyethylene repeating units can range from 10 to 160, preferably from 20 to 120, more preferably from 30 to 80.

The amphiphilic polymeric compound may typically have a molecular weight of from about 1000 to 9000 g/mol, preferably from 1500 to 6000 g/mol, more preferably from about 1800 to 5000 g/mol.

As mentioned above, the amphiphilic polymeric compound preferably comprises a polyethylene glycol as hydrophilic portion.

According to an embodiment, the hydrophobic portion comprises an alkyl, preferably a C$_{10}$-C$_{30}$ alkyl chain, more preferably C$_{12}$-C$_{24}$, and even more preferably C$_{14}$-C$_{20}$.

According to a preferred embodiment, the hydrophobic portion comprises a neutral or a cationic lipid, preferably a neutral lipid.

Preferably the lipid is a (C$_{12}$-C$_{20}$) fatty acid such as for instance, lauric acid, myristic acid, palmitic acid, stearic acid, arachidic acid or behenic acid, dodecenoic, tetradecenoic, hexadecenoic, hexadecadienoic, octadecenoic, octadecadienoic, octadecatrienoic, octadecatetraenoic, eicosenoic, eicosadienoic, eicosatrienoic, eicosatetraenoic, eicosapentaenoic, docosaenoic, docosadienoic, docosatrienoic, docosatetraenoic, docosapentaenoic and tetracosenoic acid. Preferred unsaturated fatty acids comprise myristoleic (cis-9-tetradecenoic), palmitoleic (cis-9-hexadecenoic), sapienic (cis-6-hexadecenoic), oleic (cis-9-octadecenoic), linoleic (cis-9,12-octadecadienoic), linolenic (cis-9,12,15-octadecatrienoic), gondoic (cis-11-eicosenoic), cis-11,14-eicosadienoic, cis-5,8,11-eicosatrienoic, cis-8,11,14-eicosatrienoic, cis-11,14,17-eicosatrienoic, arachidonic (cis-8,11,14,17-eicosatetraenoic) and erucic (cis-13-docosenoic) acid. Preferably the fatty acid is a saturated fatty acid. Examples of neutral polyethylene glycol modified with a fatty acid include, for instance, polyethylene glycol myristate, polyethylene glycol palmitate, polyethylene glycol stearate or polyethylene glycol arachidate.

Alternatively, the lipid linked to the PEG can be a sterol, such as cholesterol.

As a further alternative, the lipid portion can be a linear alkyl chain e.g. C$_{10}$-C$_{24}$, preferably C$_{12}$-C$_{22}$, more preferably C$_{14}$-C$_{20}$ alkyl. The alkyl chain may be linked to the PEG portion via an ether bond.

Alternatively, the amphiphilic polymeric compound may comprise two lipid residues (e.g. fatty acid residues) linked to the PEG through a glycerol group, such as PEG-DSG (1,2-distearoyl-rac-glycero-3-methyl polyoxyethylene), PEG-DPG (1,2-dipalmitoyl-rac-glycero-3-methyl polyoxyethylene) or PEG-DMG (1,2-dimyristoyl-rac-glycero-3-methyl polyoxyethylene).

Preferably, the amphiphilic polymeric compound comprises a single lipid residue, more preferably linear and even more preferably a fatty acid residue.

Examples of neutral block copolymers include, for instance, poloxamers. Poloxamers are block copolymers comprising a hydrophobic chain of oxypropylene repeating units (polypropylene glycol) and a hydrophilic chain of oxyethylene repeating units (polyethylene glycol). Typically, the hydrophobic chain of oxypropylene repeating units is delimited by two respective lateral hydrophilic chain of oxyethylene repeating units. The number of oxypropylene units may typically vary from 20 to 60, preferably from 30 to 55, more preferably from 35 to 50. The number of oxyethylene units for each of the two lateral chains may vary within the ranges indicated above, i.e. 10 to 160, preferably from 20 to 120, more preferably from 30 to 80.

Examples of cationic amphiphilic polymeric compound include, for instance cationic polyethylene lipids (CPLs) disclosed by David B. Fenske et al, "*Cationic poly(ethyleneglycol) lipids incorporated into pre-formed vesicles enhance binding and uptake to BHK cells*", Biochimica et Biophysica Acta 1512 (2001) 259272. Such CPLs include, for instance: (i) a glycerolipid anchor (e.g. distearoylphosphatidylethanolamine, DSPE), (ii) a lysine spacer containing a dansyl-label on the O-amino group, (iii) a PEG chain (e.g. PEG3400), at the distal end of which is covalently attached (iv) a positively charged headgroup, e.g. comprising a lysine residue.

As observed by the Applicant, amounts of 3% or lower of neutral or cationic amphiphilic polymeric compounds in the formulation may cause coalescence of the formed microvesicles, with the result of substantially increasing the polydispersity of microvesicles' population. Accordingly, in order to avoid or substantially limit such coalescence, the relative molar amount of the amphiphilic polymeric compound in the formulation according to the invention shall be of at least 5% or higher, preferably at least 8% or higher and even more preferably at least 9%. In certain embodiments, such molar amount can be of 20%, 25% up to e.g. 30%. Preferably the molar amount shall not exceed 50%, more preferably 40% and even more preferably it shall not exceed 30%.

As mentioned, the microvesicles of the invention preferably further include a neutral lipid, such as a neutral phospholipid and/or fatty acid.

Neutral phospholipids may include, for instance, $C_{12}$-$C_{24}$, preferably $C_{14}$-$C_{20}$, fatty acid derivatives of phosphatidylcholine or of phosphatidylethanolamine, such as dilauroyl-sn-glycero-3-phosphocholine (DLPC), dimyristoyl-sn-glycero-3-phosphocholine (DMPC), dipalmitoyl-sn-glycero-3-phosphocholine (DPPC), distearoyl-sn-glycero-3-phosphocholine (DSPC), diarachidoyl-sn-glycero-3-phosphocholine (DAPC), 1,2-dibehenoyl-sn-glycero-3-phosphocholine (DBPC) dioleoyl-sn-glycero-3-phosphocholine (DOPC), dipentadecanoyl-sn-glycero-3-phosphocholine (DPDPC), 1-myristoyl-2-palmitoyl-sn-glycero-3-phosphocholine (MPPC), 1-palmitoyl-2-myristoyl-sn-glycero-3-phosphocholine (PMPC), 1-palmitoyl-2-stearoyl-sn-glycero-3-phosphocholine (PSPC), 1-stearoyl-2-palmitoyl-sn-glycero-3-phosphocholine (SPPC), 1-palmitoyl-2-oleyl-sn-glycero-3-phosphocholine (POPC), 1-oleyl-2-palmitoyl-sn-glycero-3-phosphocholine (OPPC), dilauroyl-sn-glycero-3-phosphoethanolamine (DLPE), dimyristoyl-sn-glycero-3-phosphoethanolamine (DMPE), dipalmitoyl-sn-glycero-3-phosphoethanolamine (DPPE), diarachidoyl-sn-glycero-3-phosphoethanolamine (DAPE), distearoyl-sn-glycero-3-phosphoethanolamine (DSPE), dioleoyl-sn-glycero-3-phosphoethanolamine (DOPE), dipentadecanoyl-sn-glycero-3-phosphoethanolamine (DPDPE), 1-myristoyl-2-palmitoyl-sn-glycero-3-phosphoethanolamine (MPPE), 1-palmitoyl-2-myristoyl-sn-glycero-3-phosphoethanolamine (PMPE), 1-palmitoyl-2-stearoyl-sn-glycero-3-phosphoethanolamine (PSPE), 1-stearoyl-2-palmitoyl-sn-glycero-3-phosphoethanolamine (SPPE), 1-palmitoyl-2-oleyl-sn-glycero-3-phosphoethanolamine (POPE), 1-oleyl-2-palmitoyl-sn-glycero-3-phosphoethanolamine (OPPE).

Examples of neutral fatty acids, preferably employed in combination with any of the above neutral phospholipids, can be selected among those $C_{12}$-$C_{24}$ fatty acids previously listed, preferably palmitic or stearic acid.

In certain embodiments, the molar amount of the cationic lipid may vary from 5% to 65% of the molar amount of the total amphiphilic materials, preferably from 10% to 45%, more preferably from 12% to 30%. The neutral lipid, preferably a neutral phospholipid or a mixture of a neutral phospholipid and a fatty acid, may be present in an amount of from about 30% to 90% of the molar amount of the total amphiphilic materials, preferably from 40% to 85%, more preferably from 45% to 80%. In certain embodiments, the molar amount of the neutral lipid may vary from 50% to 85%, preferably from 60 to 80%, the molar amount of the cationic lipid may vary from 10% to 40%, preferably from 12% to 30%, and the molar amount of the amphiphilic polymeric compound can vary from 5% to 20%, preferably from 8% to 15%.

The relative molar ratio between cationic lipid and neutral/cationic amphiphilic polymeric compound may vary e.g. from 1/2 to 4/1, preferably 1/1.5 to 3.5/1, more preferably from 1/1 to 3/1, and even more preferably from 1.2/1 to 2.8/1. In certain embodiments, such molar ratio may vary from 1.5/1 to 2.5/1.

Each of the cationic lipid, neutral/cationic amphiphilic polymeric compound or neutral lipid indicated above may be employed as a single compound for the preparation of the CMV or as a respective mixture of two or more cationic lipids, neutral/cationic amphiphilic polymeric compound or neutral lipids.

Overall Charge of Microvesicles

The overall charge on the gas-filled microvesicles in the suspension can be expressed in terms of Zeta potential (or ζ-potential). The Zeta potential of microparticles can be determined, for instance, by using laser Doppler electrophoresis, e.g. by using a Nano ZSP Zetasizer (Malvern Ltd., Malvern, UK). In short, the charge or (zeta-potential) of particles is determined by measuring their velocity while they are moving due to electrophoresis. Particles and molecules that have a non-zero zeta potential will migrate towards an electrode because of the applied electric field. The particle's mobility is proportional to the field strength and its zeta-potential. By knowing the field strength, and by measuring the speed of the particles (by using laser Doppler electrophoresis), the zeta-potential of the particle can be determined (See e.g. Ref 4: Ja'Affar et al., "*Surface Charge Measurement of SonoVue™, Definity™ and Optison™: a comparison of Laser Doppler Electrophoresis and Micro-Electrophoresis*", November 2015, 41(11): 2990-3000).

Because of the positively charged components and of the neutral/cationic amphiphilic polymeric compound forming the envelope of the microvesicles, the microvesicles show a positive value of zeta-potential, typically of at least 10 mV or higher. Preferably the z-potential is of at least 12 mV and more preferably of at least 15 or higher. In certain embodiments, the z-potential is of 18 mV or higher. While there is in principle no upper limit for the z-potential measured on the microvesicles of the invention, it is in general not necessary to use microvesicles with a z-potential higher than 50 mV or in certain embodiments higher than 60 mV.

Gas

Suitable gases comprise biocompatible fluorinated gases, preferably perfluorinated gases. Fluorinated gases include materials which contain at least one fluorine atom such as, for instance, fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable gas-filled microvesicles suspensions.

The term "perfluorocarbon" includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{14}$. Particularly preferred gases are those which are in gaseous form at room temperature, including $SF_6$, $C_3F_8$ and $C_4F_{10}$.

Any of the gas can be used as a single gas or as a mixture of two or more gases.

In certain embodiment, the gas contained in the microvesicles is a mixture of a (per)fluorinated gas as indicated above with a gas (or mixture of gases) having a relatively high solubility in water, such as nitrogen, air, carbon dioxide or mixtures thereof. In the mixture, the relative volume of (per)fluorinated gas(es) may vary from 90% to 10%, preferably from 75 to 20%, more preferably from 50% to 30%.

Microfluidic Flow-Focusing Manufacturing

Calibrated gas-filled microvesicles according to the invention can be manufactured according to microfluidic flow-focusing techniques, for instance as illustrated in Ref. 1 and Ref. 2.

Figure 2:
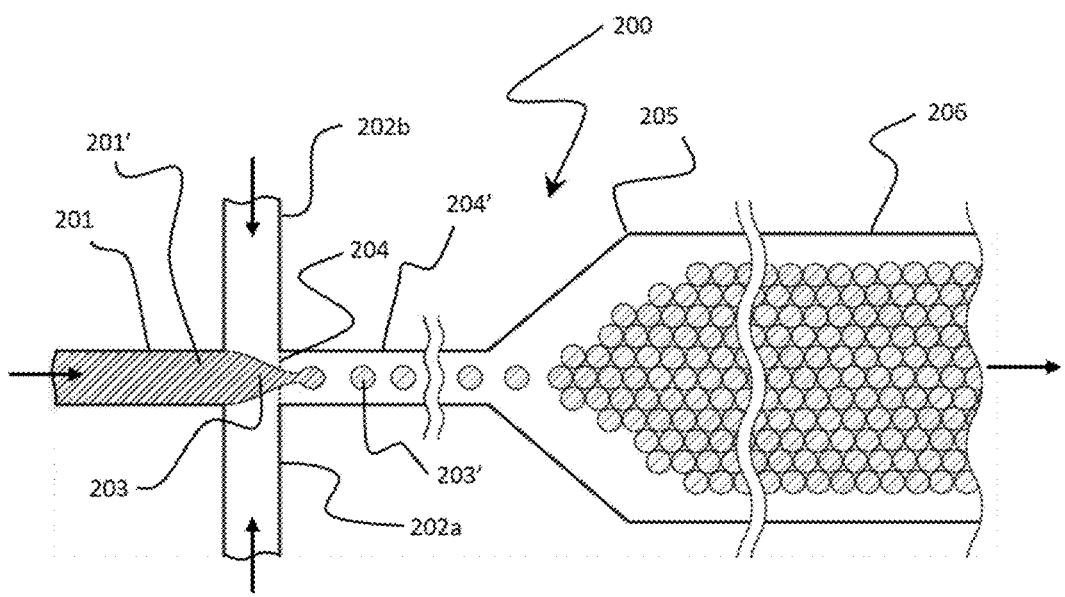
FIG. 2 shows a schematic representation of the core portion of a microfluidic flow-focusing device.

FIG. 2 shows a schematic representation of the core portion 200 of a flow-focusing device ("microfluidic chip") useful in the process of the invention. The chip comprises a first feed channel 201 for feeding the gaseous flow 201' and two additional orthogonal feed channels 202a and 202b for supplying the liquid flow comprising the amphiphilic material.

The gas flow and the two liquid flows are directed towards the contact zone 203 and then through the calibrated orifice 204, shown as a dotted line in FIG. 2. The calibrated orifice is connected to a calibrated channel 204' having preferably the same cross-section as the orifice, which is in turn connected to an initial portion 205 of the outlet channel 206.

In an alternative embodiment (not shown) the calibrated orifice 204 may be a nozzle directly connected to the initial portion 205 of outlet channel 206 i.e. without the calibrated channel in-between. The microvesicles 203' are formed in the calibrated orifice and directed, through calibrated channel 204', to the initial portion 205 of the outlet channel 206. The hydraulic diameter of the outlet channel is generally larger than the hydraulic diameter of the calibrated orifice and typically increases from the initial diameter of the calibrated orifice to the final diameter of the outlet channel 206, corresponding substantially to the hydraulic diameter of a collecting tube (not shown), connecting the flow-focusing device to a container, e.g. a sealed vial for collecting the suspension of microvesicles.

In the initial portion 205 of the outlet channel of the device and preferably also in the contact zone 203 and in the calibrated orifice 204 the temperature of the microvesicles is preferably controlled, as described e.g. in Ref. 1 or Ref. 2.

Liquid Flow

The aqueous liquid flow for preparing the calibrated gas-filled microvesicles according to the invention comprises the mixture of amphiphilic materials as above defined (i.e. a cationic lipid, a neutral or cationic amphiphilic polymeric compound and optionally a neutral lipid) at a concentration of e.g. from 5.0 to 20 mg/mL, preferably from 7.5 to 15 mg/mL, dispersed in an aqueous carrier.

The type, respective relative molar amounts and molar ratios of the cationic lipid, neutral/cationic amphiphilic polymeric compound and optional neutral lipid in the liquid flow are as indicated above.

Suitable aqueous carriers, which are preferably physiologically acceptable, comprise water (preferably sterile water), aqueous solutions such as saline (which may advantageously be balanced so that the final product for injection is not hypotonic), or solutions of one or more tonicity adjusting substances. Tonicity adjusting substances comprise salts or sugars, sugar alcohols, glycols or other non-ionic polyol materials (e.g. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose, hydroxyethyl starch or dextran.

In an alternative embodiment, an additional oil phase may be added for incorporating therapeutic hydrophobic substances into the microvesicles. To this end, two additional conduits (channels) may be provided in the device for supplying the desired oil phase, as described for instance by Ref. 1 or Ref. 2. The formed gas-filled microvesicles will thus have a film of oil disposed at the interface between gas and the stabilizing layer of amphiphilic material, which can be loaded with a desired therapeutic agent. Suitable oils may include any biocompatible oil which is liquid at room temperature including, for instance, mono-, di- or tri-esters of glycerol with saturated or unsaturated ($C_2$-$C_{18}$) alkyl chains (including homo- or hetero-allkylesters), such as glycerol monobutyrin, glycerol monolinoleate, 1,2-dihexanoyl glycerol, 1,2 dioctanoyl glycerol, 1,2-dioleyl-sn-glycerol, triacetin, tributyrin, tricaproin, tricaprylin, tricaprin, and mixtures thereof; or natural oils such as soya oil, olive oil, safflower seed oil, sunflower seed oil, peanut oil and mixtures thereof.

Gas Flow

The freshly formed microvesicles comprise a gas selected among those previously indicated. Preferably the gas is a mixture of a gas highly soluble in water ("HS gas") and of a gas with low solubility in water ("LS gas"), as described in Ref. 2.

Examples of HS gases include nitrogen, air, and carbon dioxide, this latter being particularly preferred because of its higher solubility in water.

Suitable LS gases are fluorinated gases, preferably perfluorinated gases, such as, those previously illustrated.

Figure 3:
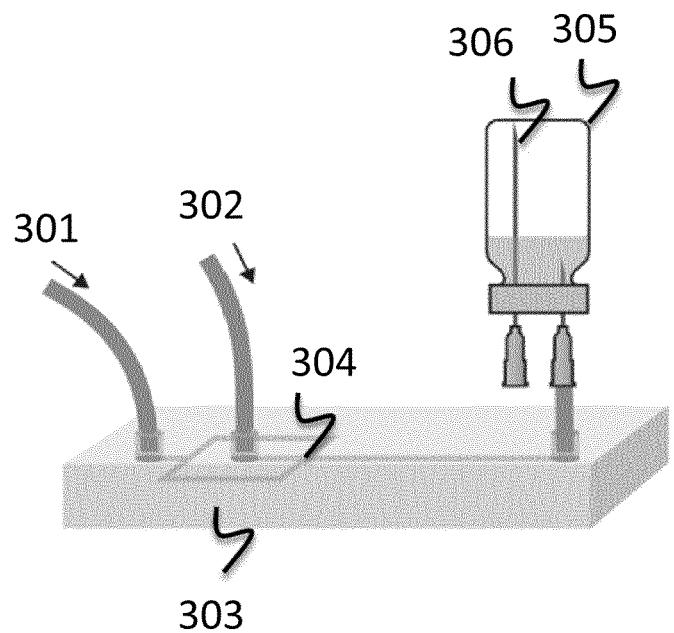
FIG. 3 shows an exemplary schematic drawing of a device useful for the manufacturing process of calibrated gas-filled microvesicles.

In a preferred embodiment of the invention, gas-filled microvesicles comprising $CO_2/C_4F_{10}$ in a volume ratio of from 80/20 to 90/10, e.g. 85/15 can be prepared with a gas-mixing device similar to the one schematically illustrated in FIG. 3.

FIG. 3 shows an example of a microfluidic flow-focusing device used to produce calibrated microvesicles. A gas flow 302 (comprising e.g. a mixture of $C_4F_{10}$ and $CO_2$) and a liquid flow 301 (comprising an amphiphilic material, e.g. a phospholipid, fatty acid or mixtures thereof), are supplied to microfluidic chip 303 to produce microvesicles through orifice 304. The microvesicles suspension is collected in a vial 305, which is preferably prefilled with a gas (e.g. $C_4F_{10}$) at ambient pressure. A venting device (e.g. a needle 306) is preferably used to equalize the overpressure generated by the liquid filling of the vial. At the end of the collection of the microvesicles suspension, the venting device is preferably removed, and the container is preferably sealed to avoid further gaseous exchange with the external atmosphere.

In certain embodiments, a suspension of gas-filled microvesicles according to the invention may be obtained by:
providing (i) a gaseous flow and (ii) an aqueous liquid flow comprising a cationic lipid and a neutral or cationic amphiphilic polymeric compound as defined above;
directing said gaseous flow and said liquid flow through respective inlet channels towards a contact zone;
directing said gaseous flow and said liquid flow from the contact zone through a calibrated orifice to obtain an aqueous suspension comprising said gas-filled microvesicles;
directing said suspension of gas-filled microvesicles towards an outlet channel; and
collecting said suspension of gas-filled microvesicles.

According to an embodiment of this invention, after the collection phase, the calibrated microvesicles obtained through the microfluidic flow-focusing method may be used as such for the subsequent application. In an alternative embodiment, the suspension of gas-filled microvesicles may be subjected to a washing step, in order to remove possible amphiphilic material not included in the stabilizing layer of the microvesicles and possible residual additive compounds. Suitable techniques for performing the above additional washing step include, for instance, centrifugation, filtration, microvesicles sorting and decantation.

In an embodiment, a freeze-drying protecting component can be added to the obtained suspension of CMV, as described e.g. in WO2020/260420 (Ref. 5) or WO2020/260423 (Ref. 6). Alternatively, the freeze-drying protecting component can be added to the liquid flow comprising the amphiphilic compounds, as described above, during the preparation of the microvesicles by microfluidic technique. Suitable freeze-drying components include, for instance, a polyglycol, such as polyethylene glycol (e.g. PEG4000), or a mixture of a polyglycol (e.g. polyethylene glycol with a polyol (e.g. sorbitol or xylitol) or a saccharide (e.g. sucrose). The obtained suspension of CMV may then undergo a subsequent freeze-drying step, to obtain a freeze-dried product as described in the above cited Ref. 5 or Ref. 6. The freeze-dried product can then be stored for a relatively long period before being reconstituted with a physiologically acceptable liquid (e.g. saline) in the presence of a biocompatible fluorinated gases as defined above under gentle agitation, to provide the suspension of CMV.

Size Distribution and Concentration of CMV

Depending on the parameters of the manufacturing process, the components of the microvesicles' stabilizing layer and the design of the device, the calibrated microvesicles may be obtained with relatively narrow size distribution around any desired mean diameter, e.g. from 2 to 8 µm, preferably from 3 to 6 µm.

The size distribution of CMV is typically characterized by a geometric standard deviation (GSD) value of at least 1.25 or lower, preferably of 1.20 or lower, more preferably of 1.15 or lower, down to e.g. 1.05.

The "geometric standard deviation" (GSD) generally provides a suitable value for characterizing the width of the size distribution in a population of particles (gas-filled microvesicles in the specific case). A population of particles with a broad range of sizes will thus has a larger GSD value than one in which the particles sizes are narrowly distributed around a mean value (i.e. relatively similar in size).

FIG. 1 shows an example of a size distribution graph (by volume) of a population of gas filled microvesicles which can be obtained with a commercial particle analyser instrument (e.g. Coulter Counter Multisizer 3, equipped with the Multisizer 3 software), by determining the volume of gas for each of its channels, each channel corresponding to a predetermined diameter of the microvesicles (e.g. with increments of 0.1 microns). By the determination of the number of calibrated gas-filled microvesicles in the suspension, their respective diameter and volume distribution in a selected size range (e.g. between 3 µm and 6 µm for a 4.5 µm CMV mean diameter), it is possible to calculate the GSD of a CMV distribution, by using the following Equation 1:

$$GSD = e^{\sqrt{\frac{\sum[n_i(\ln x_i - \ln \bar{x})^2]}{\sum n_i}}} \qquad \text{Eq. 1}$$

Where:
$n_i$=percentage of volume of gas (with respect to the total one) entrapped in the microvesicles measured for the ith channel
$x_i$=volume of the microvesicles in the $i^{th}$ channel, where $$x_1 = d_i^3 \cdot \pi/6. \qquad \text{Eq. 1.1}$$

($d_i$=diameter of the microvesicle in the $i_{th}$ channel center)
$\bar{x}$=geometric mean of the volume of the microvesicles in the selected range, where:

$$\bar{x} = 10\left[\frac{\sum(n_i \cdot \log x_i)}{\sum n_i}\right]. \qquad \text{Eq. 1.2}$$

Among the various commercially available analytical devices, the Coulter Counter Multisizer 3, equipped with the Multisizer 3 software, is capable of calculating and providing such GSD value as defined above.

For instance, for a particles size distribution having a mean diameter (in number) of 4 µm, a GSD value of 1.2 indicates that about the 50% of CMV have a size between 2.5 and 5 µm; a GSD of 1.05-1.08 (<1.1) indicates that about the 95-90% of CMV have a size comprised between 2.5 and 5 µm.

The concentration of CMV in the suspension (particularly upon production with microfluidic flow-focusing technique) is typically of at least $2.0 \times 10^8$ CMV/mL or higher, preferably at least $2.1 \times 10^8$ CMV/mL, more preferably at least $2.3 \times 10^8$ CMV/mL, up to e.g. $1 \times 10^9$ CMV/mL.

The expression "microvesicles concentration" as used herein refers to the number of CMV in a volume unit, determined using a Coulter Counter apparatus, i.e. number of CMV per mL of suspension.

Use of Microvesicles

The microvesicles of the invention may be used in a variety of biomedical diagnostic and/or therapeutic techniques, including in particular ultrasound imaging and therapeutic applications.

Diagnostic methods include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including, for instance, fundamental and harmonic B-mode imaging, pulse or phase inversion imaging, Power modulation Contrast Mode, Pulse Wave Doppler, Color Doppler, Power Doppler, Maximum Intensity Projection, Ultrafast Imaging, Ultrasound Localization Microscopy, Vector Flow Imaging and Destruction Replenishment Quantification; if desired three-dimensional imaging techniques may be used.

Microvesicles according to the invention may typically be administered in a concentration of from about 0.01 to about 1.0 µL of gas per kg of patient, depending e.g. on their respective composition, the tissue or organ to be imaged and/or the chosen imaging technique. This general concentration range may of course vary depending on specific imaging applications, e.g. when signals can be observed at very low doses such as in colour Doppler or power pulse inversion.

In an embodiment said method of diagnosing comprises
(i) administering to a patient a suspension of CMV as defined above; and
(ii) detecting an ultrasound signal from a region of interest in said patient.

Possible other diagnostic imaging applications include scintigraphy, light imaging, and X-ray imaging, including X-ray phase contrast imaging.

Another aspect of the invention relates to the use in a method of therapeutic treatment of a suspension CMV as above defined, including in-vitro, ex-vivo and/or in vivo.

In-vitro or ex-vivo methods include, for instance, loading of genetic material (such as DNA, SIRNA and similar) or cell transfection or DNA transfection, e.g. by sonoporation. In vitro or ex-vivo therapeutic applications can be used, for instance, to treat neurological disorders with a focus on Parkinson's disease, Huntington's disease, Alzheimer's disease, ALS, stroke and in cardiovascular therapy.

In-vivo therapeutic treatments include any method of treatment which comprises the combined use of ultrasounds and gas-filled microvesicles either as such (e.g. in ultrasound mediated thrombolysis, high intensity focused ultrasound ablation, blood-brain barrier permeabilization, immunomodulation, neuromodulation, radiosensitization) or in combination with a therapeutic agent (i.e. ultrasound mediated delivery, e.g. for the delivery of a drug or bioactive compound to a selected tissue, organ or region of interest, such as in tumor treatment, gene therapy, infectious diseases therapy, metabolic diseases therapy, chronic diseases therapy, degenerative diseases therapy, inflammatory diseases therapy, immunologic or autoimmune diseases therapy or in the use as vaccine), whereby the presence of the gas-filled microvesicles may provide a therapeutic effect itself or is capable of enhancing the therapeutic effects of the applied ultrasounds, e.g. by exerting or being responsible to exert a biological effect in vitro and/or in vivo, either by itself or upon specific activation by various physical methods (including e.g. ultrasound mediated delivery of therapeutic material).

Microvesicles according to the invention can typically be administered for therapeutic purposes in a concentration of from about 0.01 to about 5.0 µL of gas per kg of patient, depending e.g. on their respective composition, the type of subject under treatment, the tissue or organ to be treated and/or the therapeutic method applied.

In an embodiment said method of ultrasound therapeutic treatment comprises:
(i) administering to a patient a suspension of CMV as defined above;
(ii) identifying a region of interest in said patient to be submitted to a therapeutic treatment, said region of interest comprising said suspension of CMV; and
(iii) applying an ultrasound beam for therapeutically treating said region of interest;
whereby said ultrasound therapeutic treatment is enhanced by the presence of said suspension of CMV in said region of interest.

As illustrated in the examples, the overall positive charge on the CMV allows to effectively bind molecules having an overall negative charge to said CMV, typically by electrostatic interactions. According to an embodiment, the CMV can thus be suitably bound to materials, in particular therapeutically effective materials, bearing an overall negative charge such as, for instance, genetic material or drugs, including e.g. DNA, mRNA, saRNA, plasmids or nanoplasmids. The CMV of the invention bound to such therapeutically effective material can thus be used in therapeutic methods for improving the delivery of such therapeutically effective material.

In another embodiment said method of ultrasound therapeutic treatment thus comprises:
(i) administering to a patient a suspension of CMV as defined above which are bound to a therapeutically effective material bearing an overall negative charge;
(ii) identifying a region of interest in said patient in need of said therapeutic treatment, said region of interest comprising said suspension of said bound CMV; and
(iii) applying an ultrasound beam for therapeutically treating said region of interest, said treating comprising the release of the therapeutically active material in the region of interest.

The following examples will help to further illustrate the invention.

EXAMPLES

Materials and Methods

DSPC: 1,2-distearoyl-sn-glycero-3-phosphocholine (Sygena)
DSTAP: 1,2-stearoyl-3-trimethylammonium-propane (chloride salt) (Avanti Polar Lipids/Merck)
DOTAP: 1,2-dioleoyl-3-trimethylammonium-propane (chloride salt) (Avanti Polar Lipids/Merck)

DDAB: Dimethyldioctadecylammonium (Bromide Salt) (Avanti Polar Lipids/Merck)

DSG-PEG2000: distearoyl-rac-glycerol-PEG2K (Avanti Polar Lipids/Merck)

DMG PEG2000: dimyristoyl-rac-glycerol-PEG2K (Avanti Polar Lipids/Merck)

Chol-PEG2000: mPEG2000-cholesterol (Creative PEGworks)

DPPE-PEG5000: 1,2-dipalmitoyl-sn-glycero-3-phosphoethanolamine-N-[methoxy(polyethylene glycol)-5000], ammonium salt (Lipoid) 5727 g/mol DSPE-PEG2000: 1,2-distearoyl-sn-glycero-3-phosphoethanolamine-N-[methoxy(polyethylene glycol)-2000] (ammonium salt) (Genzyme) 2787 g/mol PEG40S/MYRJ52: Polyoxyethylene (40) monostearate (Sigma) 2046 g/mol PEG100S/MYRJ59: Polyethylene glycol (100) monostearate (Sigma) 4666 g/mol Pluronic F68: Polyoxyethylene-polyoxypropylene block copolymer (Sigma) 8350 g/mol Size distributions and concentrations of CMV preparations were measured with a Coulter Counter Multisizer 3 (Beckman Coulter, Fullerton, CA) using an aperture tube with a diameter of 30 μm allowing a measurable size range of 0.7-18 μm.

The Zeta potential of CMV was measured using a Nano ZSP Zetasizer (Malvern Ltd., Malvern, UK), which allows for the measurement of Z-potential by laser Doppler electrophoresis. 50 μL of cationic CMV were diluted in 1 mL saline 1 mM and injected in the disposable Folded Capillary Cell (DTS1070). The measurement was set in "automatic mode" and the equilibration time of the suspension in the measurement cell was of 20 seconds.

Example 1

Preparation of Gas-Filled Microvesicles with Cationic Lipids

Gas-microvesicles were prepared using a commercially available microfluidic flow-focusing device (CU4553.007 N30 design, Micronit Microfluidics, NL), mounted in a commercially available chip holder (Micronit microfluidics, Fluidic Connect PRO Chip Holder with 4515 Inserts). The microvesicles formation channel had a width of 19 μm. The chip and its holder were positioned in an optically transparent temperature controlled water bath that was mounted on an inverted microscope equipped with a 10 times magnification objective (Olympus, LMPLAN 20×) and a CCD camera (Lumenera, LM156M). The temperature of the thermostatic bath was set between 50° C. and 70° C., above the transition temperature of the lipids mixture used for preparing the microvesicles.

The gas-filled microvesicles, comprising $CO_2/C_4F_{10}$ in a volume ratio of 85/15, were prepared with a gas-mixing device like the one schematically illustrated in FIG. 3.

Briefly, two gas containers were filled with $CO_2$ and $C_4F_{10}$, respectively. The gas flow of each gas was regulated by respective mass flow controllers: (i) EL-Flow: F200CV-002-RAD-11-K, for the $CO_2$ and (ii) Low-AP-Flow: F-200DV-RAD-11-Z for $C_4F_{10}$ (both gas controllers from Bronkhorst, Ruurlo, The Netherlands). The mass flow controllers were controlled by a customized software program implemented in Matlab (Mathworks), which was installed on a personal computer, in order to set and keep the desired mixing ratio. A pressure sensor (PSE530-M5-L; SMC Corp., Tokyo, Japan) measured the actual pressure in the gas mixture in the outlet channel leading to the microfluidic chip; a gas pressure of 2 bars was used for the formation of the microvesicles. The liquid co-flow rate was controlled by using a separate mass flow controller (Mini Cori Flow: M13V14I-MAD-11-K-S; Bronkhorst, Ruurlo, The Netherlands). A liquid co-flow rate of 150-180 μL/min was used to operate the flow-focusing device in the jetting regime and produce microvesicles with a diameter (mode) of 3 to 5 μm, depending on the materials employed.

The lipid materials were dispersed (at concentrations of 15 mg/mL) in saline (0.9% NaCl) at 60° C. under stirring for 30 minutes and the dispersion was then sonicated by using a tip sonicator (Branson Sonifier 250) to homogenously disperse the material. The preparations were then filtered using a polycarbonate filter (0.45 μm pore size), cooled down to room temperature and degassed.

A total of six formulations according to the invention (Preparations 01 to 06) and two comparative formulations (Preparations C1 and C2) were prepared. In particular, preparations 01 to 06 comprise a cationic lipid, a neutral amphiphilic polymeric compound and a neutral phospholipid, while comparative preparations C1 and C2 comprise a cationic lipid, a negatively charged amphiphilic polymeric compound and a neutral phospholipid. The composition and relative molar ratios of the amphiphilic materials in the respective preparations are illustrated in Table 1.

TABLE 1

| Materials (and compositions) for the preparation of CMV | | | | | |
|---|---|---|---|---|---|
| Cationic lipid | | Amphiphilic polymeric compound | | Neutral lipid | |
| Prep Compound | Mol (%) | Compound | Mol (%) | Compound | Mol (%) |
| 01 DSTAP | 15 | PEG40-stearate | 10 | DSPC | 75 |
| 02 DSTAP | 25 | PEG40-stearate | 10 | DSPC | 65 |
| 03 DOTAP | 25 | PEG40-stearate | 10 | DSPC | 65 |
| 04 DDAB | 15 | PEG40-stearate | 10 | DSPC | 75 |
| 05 DSTAP | 15 | PEG100-stearate | 10 | DSPC | 75 |
| 06 DSTAP | 15 | F68 | 10 | DSPC | 75 |
| C1 DSTAP | 15 | DSPE-PEG2000 | 10 | DSPC | 75 |
| C2 DSTAP | 15 | DPPE PEG5000 | 10 | DSPC | 75 |

Characteristics (mean size, size distribution, concentration and Zeta potential) of the obtained microvesicles preparations, measured as illustrated above, are provided in the table 2 below.

TABLE 2

Characteristics of cationic calibrated microvesicles

| Prep | Dv (μm) | GSD | CMV/mL | MVC (μL/mL) | Z- potential (mV) |
|---|---|---|---|---|---|
| 01 | 4.73 | 1.08 | $4.2 \times 10^8$ | 23.0 | 14 |
| 02 | 4.3 | 1.184 | $4.3 \times 10^8$ | 17.8 | 16 |
| 03 | 4.7 | 1.132 | $3.9 \times 10^8$ | 18.9 | 28 |
| 04 | 4.6 | 1.064 | $4.4 \times 10^8$ | 22.1 | 20 |
| 05 | 4.5 | 1.089 | $4.3 \times 10^8$ | 19.6 | 17 |
| 06 | 3.3 | 1.082 | $4.2 \times 10^8$ | 6.9 | 35 |
| C1 | 5.05 | 1.123 | $1.0 \times 10^8$ | 6.2 | −7 |
| C2 | 4.73 | 1.095 | $4.2 \times 10^8$ | 22.4 | 6 |

Example 2

Plasmid Binding Assays
YOYO-1 Labelling

Eighty (80) μL of a diluted solution (25 μM) of YOYO-1 (Molecular probes #Y-3601) were added under gentle mixing to 320 μL of a 800 μg/mL DNA solution (Plasmid luciferase, from Plasmid Factory).

The fluorescence of the complex as a function of DNA concentration was determined on diluted samples (from 1 to 50 μg/mL of DNA) in a black 96-wells plate (Wallac) using Cytation5 imaging reader (Biotek) with 485 nm for excitation filter and 535 nm for emission filter (YOYO-1 λexc: 491 nm-λem: 509 nm).

DNA Adsorption on Cationic Calibrated Microvesicles 10 to 40 μg of DNA/YOYO-1 was placed in a 5 ml-glass tube. A volume of about 1 mL the preparation of gas filled microvesicles prepared according to Example 1 was washed twice by centrifugation (64 g—6 min); then, the suspension volume was adjusted to 1 mL with saline (to have a final concentration of about $4 \times 10^8$ CMV/mL) and added to the DNA solution. After gentle mixing (15 min), the microvesicles suspension with DNA was washed by centrifugation (64 g—6 min), the infranatant (~0.9 mL) was removed and the fluorescence of the solution was measured as the standard curve (100 μL/well, 2 measures per sample). The DNA concentration in the infranatant was calculated and the DNA bound to microvesicles was determined by difference with respect to the initial amount, to provide the binding yield of DNA, as illustrated in table 3. The microvesicles comprising the bound DNA (supernatant) were redispersed in 1 mL saline solution, and their zeta-potential was measured as described above. Results are reported in table 3 as well.

TABLE 3

Binding of plasmid to cationic calibrated microvesicles

| Preparation | Initial amount of loaded DNA | Binding yield | Zeta potential of cationic CMV + DNA |
|---|---|---|---|
| 01 | 10 | 92% | −4 |
|  | 20 | 56% | −15 |
|  | 30 | 34% | −26 |
|  | 40 | 24% | −21 |
| 02 | 10 | 95% | −8 |
|  | 20 | 95% | −8 |
|  | 30 | 66% | −16 |
|  | 40 | 57% | −16 |
| 04 | 10 | 94% | −17 |
|  | 20 | 64% | −22 |
|  | 30 | 42% | −16 |
|  | 40 | 31% | −14 |
| 05 | 20 | 49% | −26 |
|  | 30 | 49% | −32 |
|  | 40 | 48% | −37 |
| C1 | 10 | 0% | −2 |
|  | 20 | 0% | −1 |
|  | 30 | 0% | −2 |
|  | 40 | 0% | −2 |
| C2 | 10 | 0% | −0.5 |
|  | 20 | 0% | 0.5 |
|  | 30 | 0% | −0.2 |
|  | 40 | 0% | 0.5 |

As inferable from the above table, cationic microvesicles according to the invention are capable of binding substantial amounts of DNA, differently from comparative cationic preparations comprising a negatively charged pegylated lipid.

Example 3

Preparation of Further Gas-Filled Microvesicles with Cationic Lipids and Different Amphiphilic Polymeric Compounds The preparation of example 1 was repeated by using different amphiphilic polymeric compounds and different molar amounts of such compounds.

A total of nine formulations were prepared. The effects of various amphiphilic polymeric compounds and respective molar amounts on the % of coalescence of gas-filled microvesicles has been evaluated.

Figure 4:
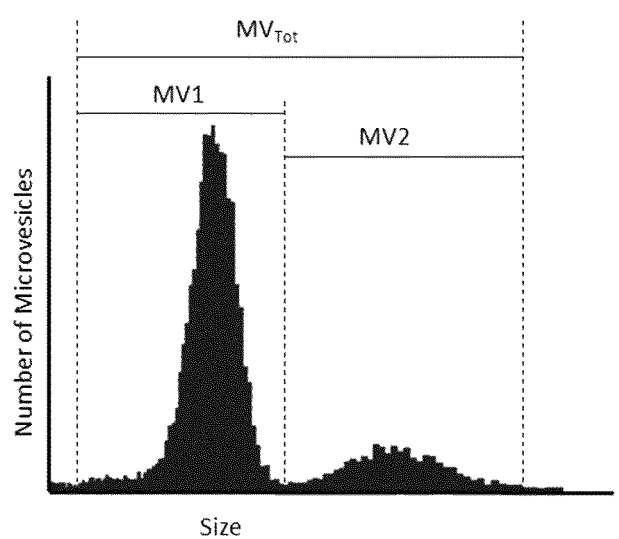
FIG. 4 represents a schematic illustration of a size distribution of gas-filled microvesicles for the calculation of the percentage of coalescence.

The percentage of coalescence can be determined by calculating the total number of microvesicles from the secondary peak (MV2) of the size distribution (as illustrated in FIG. 4), corresponding to the coalesced microvesicles, and dividing it by the total number of microvesicles (i.e. those of primary peak MV1 and of secondary peak MV2). A percentage of 0% of coalescence indicates that no coalescence is observed, and thus there is no impact on the size distribution of the preparation. On the other side, increasing values of coalescence indicate that larger microvesicles are formed due to coalescence, which may negatively impact the size distribution of the preparation, in particular with the formation of a sub-population of larger microvesicles.

The percentage of coalescence for each preparation, as well as for preparation 01 of Example 1, is reported in the last column of table 4.

TABLE 4

Materials (and compositions) for the preparation of CMV

| Prep | Cationic lipid Compound | Mol (%) | Amphiphilic polymeric compound Compound | Mol (%) | Neutral lipid Comp. | Mol (%) | % of Coalescence |
|---|---|---|---|---|---|---|---|
| A | DSTAP | 15 | PEG40-stearate | 3 | DSPC | 82 | 10% |
| B | DSTAP | 15 | PEG40-stearate | 7.5 | DSPC | 77.5 | 4% |
| 01 | DSTAP | 15 | PEG40-stearate | 10 | DSPC | 75 | 0% |
| C | DSTAP | 15 | DSG-PEG2000 | 10 | DSPC | 75 | 12% |
| D | — | — | DMG-PEG2000 | 3 | DSPC | 97 | 12% |
| E | — | — | DMG-PEG2000 | 10 | DSPC | 90 | 5% |
| F | — | — | DMG-PEG2000 | 30 | DSPC | 70 | 0% |
| G | DSTAP | 15 | DMG-PEG2000 | 30 | DSPC | 55 | 0% |
| H | — | — | Chol-PEG2000 | 10 | DSPC | 90 | 5% |
| I | — | — | Chol-PEG2000 | 20 | DSPC | 80 | 0% |
| L | DSTAP | 15 | Chol-PEG2000 | 20 | DSPC | 65 | 0% |

As illustrated from the results of the above table, amounts of 3% or lower of amphiphilic polymeric compounds result in a non-negligible coalescence of the microvesicles. On the other hand, the coalescence can be reduced by increasing the molar amounts of said polymeric compound, up to a substantial absence of said coalescence when a sufficient amount of amphiphilic polymeric compound is present in the formulation. For compositions G and L, a respective Z-potential of 21.3 mV and 21.7 mV has been measured.

REFERENCES

Ref. 1: WO2018/041906
Ref. 2: WO2019/170606
Ref. 3: Wang et al., "Cationic versus Neutral Microbubbles for Ultrasound-mediated Gene Delivery in Cancer", Radiology: Volume 264: Number 3 Sep. 2012, pp 721-732
Ref 4: Ja'Affar et al., "Surface Charge Measurement of SonoVue™, Definity™ and Optison™: a comparison of Laser Doppler Electrophoresis and Micro-Electrophoresis", November 2015, 41(11): 2990-3000
Ref 5: WO2020/260420
Ref 6: WO2020/260423

The invention claimed is:

1. A suspension of calibrated gas-filled microvesicles with a stabilizing envelope comprising an amphiphilic material, wherein:
   said amphiphilic material comprises a cationic lipid and a neutral or cationic amphiphilic polymeric compound, said amphiphilic polymeric compound comprising a respective hydrophilic and a hydrophobic portion and being present in a molar amount higher than 3%; and
   said gas-filled microvesicles have a geometric standard deviation (GSD) value of at least 1.25 or lower.

2. The suspension according to claim 1 wherein the cationic lipid is a saturated or unsaturated hydrocarbon chain linked to an ammonium group.

3. The suspension according to claim 2 wherein the cationic lipid is a cationic phospholipid, an ammonium moiety comprising a fatty acid residue an alkyl residue or an alkyloxy residue.

4. The suspension according to claim 3 wherein said cationic lipid is a ethyl phosphatydilcholine comprising a $C_8$-$C_{24}$ fatty acid, a $C_8$-$C_{24}$ fatty acid trimethylammonium or a $C_8$-$C_{24}$ alkyl or alkyloxy moiety bound to a quaternary or to a protonated tertiary ammonium group.

5. The suspension according to claim 1 wherein said amphiphilic polymeric compound comprises a polyethylene glycol.

6. The suspension according to claim 1 wherein said amphiphilic polymeric compound has a molecular weight of from 1000 to 9000 g/mol.

7. The suspension according to claim 1 wherein the cationic lipid is in an amount of from 5% to 65% of the total molar amount of the amphiphilic material.

8. The suspension according to claim 1 wherein the amphiphilic polymeric compound is in an amount of at least 5% of the total molar amount of the amphiphilic material.

9. The suspension according to claim 1 wherein the amphiphilic polymeric compound is in an amount of at least 8% of the total molar amount of the amphiphilic material.

10. The suspension according to claim 1, wherein said amphiphilic polymeric compound is an ester of polyethylene glycol with a $C_{12}$-$C_{24}$ fatty acid.

11. The suspension according to claim 1, wherein said amphiphilic polymeric compound is a block copolymer comprising oxypropylene repeating units and oxyethylene repeating units.

12. The suspension according to claim 1 wherein said amphiphilic material further comprises a neutral lipid.

13. The suspension according to claim 12, wherein said neutral lipid is a $C_{12}$-$C_{24}$ fatty acid derivative of phosphatidylcholine or of phosphatidylethanolamine.

14. The suspension according to claim 12 wherein said neutral lipid is present in an amount of from 30% to 90% of the total molar amount of the amphiphilic material.

15. The suspension according to claim 1 wherein said suspension of gas-filled microvesicles has a Z-potential of 10 mV or higher.

16. The suspension according to claim 1 further comprising a negatively charged therapeutically active material bound to the surface of the microvesicle.

17. The suspension according to claim 16, wherein said therapeutically active material comprises genetic material.

18. The suspension according to claim 17, wherein said genetic material comprises DNA, mRNA, saRNA, plasmids or nanoplasmids.

* * * * *